(12) United States Patent
Thauront et al.

(10) Patent No.: US 6,312,582 B1
(45) Date of Patent: Nov. 6, 2001

(54) FORMATION TEREPHTHALIC ACID BY ELECTROCHEMICAL ACIDIFICATION OF A SODIUM TEREPHTHALATE SOLUTION

(75) Inventors: Jacques Thauront, La Garenne-Colombes; Sylvain Durecu, Villers les Nancy, both of (FR); Jean-Paul Wiaux, Croix de Rozon (CH); Bach-Tuyêt Lam, Chaligny (FR)

(73) Assignee: Tredi, Paris (FR)

( * ) Notice: Subject to any disclaimer, the term of this patent is extended or adjusted under 35 U.S.C. 154(b) by 0 days.

(21) Appl. No.: 09/498,483

(22) Filed: Feb. 4, 2000

Related U.S. Application Data

(63) Continuation of application No. PCT/FR98/01722, filed on Jul. 31, 1998.

(30) Foreign Application Priority Data

Aug. 6, 1997 (FR) .................................................. 97 10095

(51) Int. Cl.[7] .................................................... C25B 3/00
(52) U.S. Cl. ........................................... 205/442; 205/440
(58) Field of Search ..................... 205/440, 442

(56) References Cited

U.S. PATENT DOCUMENTS

| | | | |
|---|---|---|---|
| 4,092,230 | * 5/1978 | Norton | 204/180 P |
| 4,093,528 | * 6/1978 | Wynkoop et al. | 204/180 P |
| 5,290,404 |   3/1994 | Toomey et al. | 204/72 |
| 5,545,746 | * 8/1996 | Benzaria et al. | 560/78 |

FOREIGN PATENT DOCUMENTS

| | | |
|---|---|---|
| 0573042 | 12/1993 | (EP) . |
| 2697839 | 5/1994 | (FR) . |

* cited by examiner

*Primary Examiner*—Edna Wong
(74) *Attorney, Agent, or Firm*—Venable; Michael A. Gollin

(57) ABSTRACT

A method for recuperating from saponification products of alkaline polyterephthalate with soda where both terephthalate ions are in acid form and the sodium ions are in the form of soda is disclosed. In this method the sodium terephthalate solution resulting from dissolving the saponification products are subjected to a step of electrochemical pre-acidification to bring the pH to 4 to 7. Thereafter an electrochemical acidification step by electrolysis is undertaken to precipitate the terephthalic acid in the anode section and recuperate the soda in the cathode section which can be recycled.

19 Claims, 2 Drawing Sheets

DIAGRAM OF ELECTROLYSER

FIGURE 1. DIAGRAM OF ELECTROLYSER
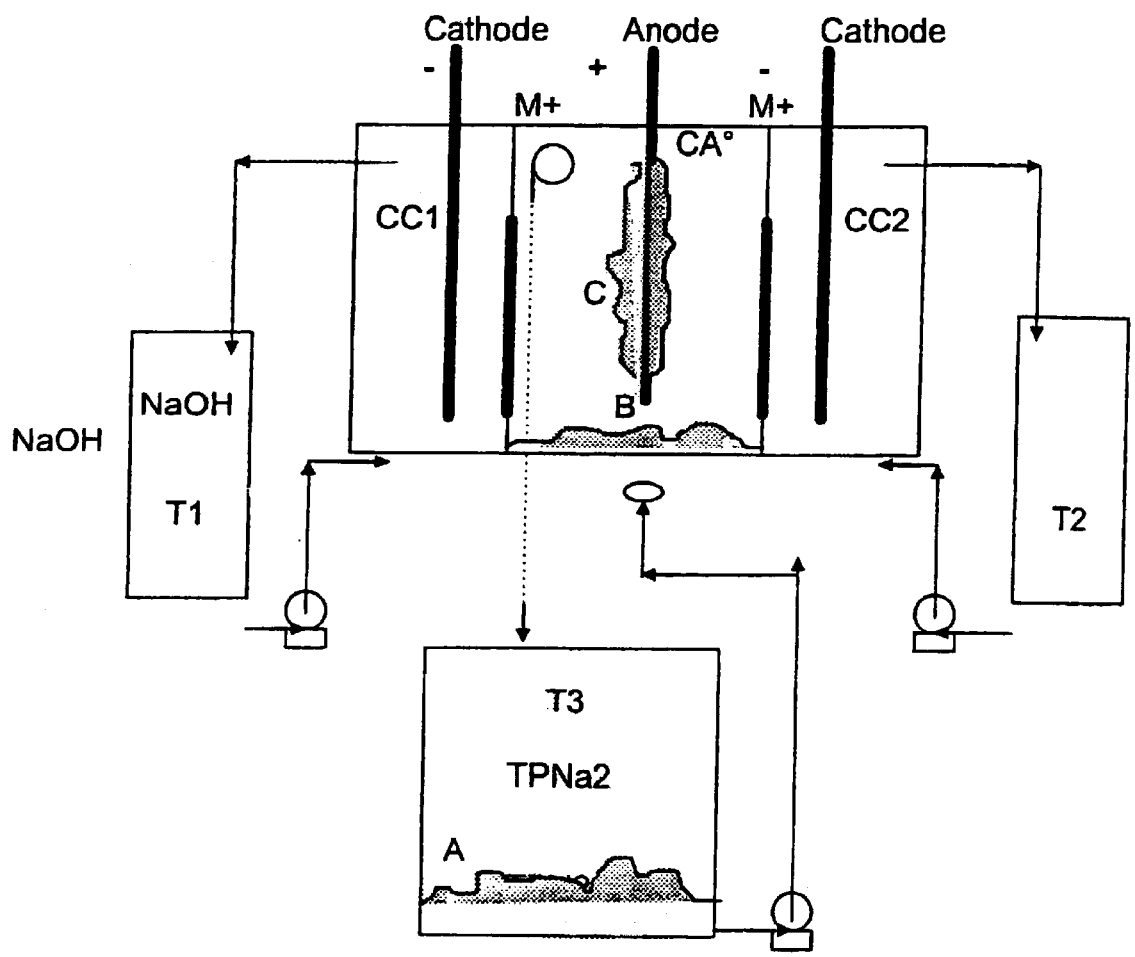

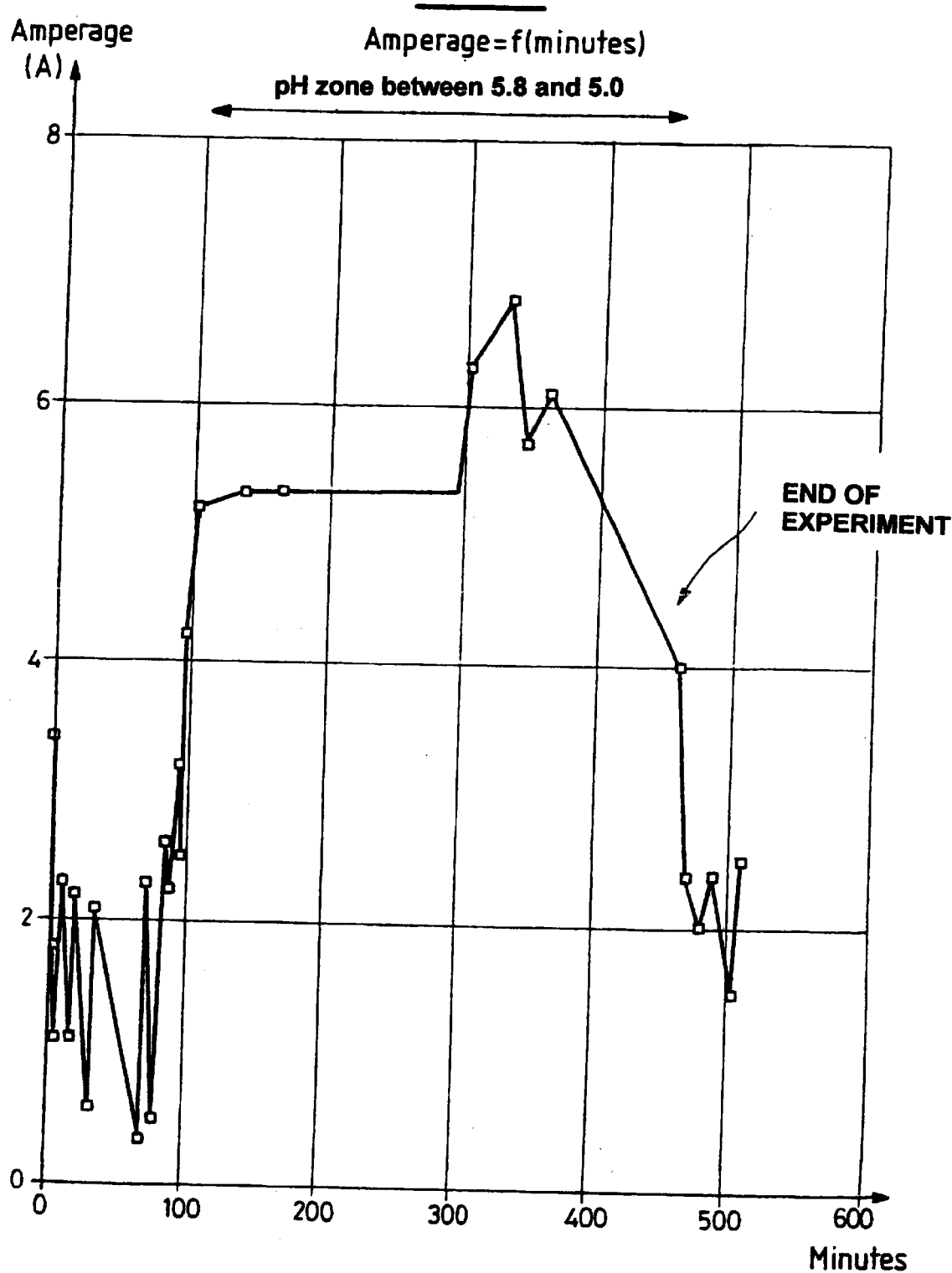

FORMATION TEREPHTHALIC ACID BY ELECTROCHEMICAL ACIDIFICATION OF A SODIUM TEREPHTHALATE SOLUTION

This appln is a continuation of PCT/FR98/01722 filed Jul. 31, 1998.

The invention relates to a process for recovering aromatic polycarboxylic acids such as terephthalic acid (hereinafter abbreviated to $H_2TP$) from a solution of alkali metal salts of such aromatic polycarboxylic acids, in particular from a solution of sodium terephthalate ($Na_2TP$).

$Na_2TP$ is a product which is available or potentially available on the market in large quantities, for example by alkaline saponification of industrial polyol polyterephthalates, in particular glycol. Polyterephthalates (PTEs) are used in large quantities in the food industry, in particular for the production of plastic bottles, or in other industries, for example for the production of support membranes for photographic films or the like. Examples of such saponification processes which can be mentioned are those described in British patent GB 822 834, U.S. Pat. No. 3,544,622 and French patents FR-A-2 672 049 and FR-A-2 697 839. The $Na_2TP$ produced (obtained as a solution or as an aqueous solution) must then be transformed to $H_2TP$ which can in its turn be recycled to the step for producing new batches of PTE by polymerisation with fresh batches of polyol.

The transformation of $Na_2TP$ to $H_2TP$ is not without its difficulties, however, even if it is obtained in the practically pure state, either because of a modification in the conditions under which saponification is carried out or as a result of previous purification operations. Clearly, care must be taken in all cases to avoid the use of excessive amounts of water. Even when very pure, $Na_2TP$ solutions are highly alkaline, if only because of their concentrations. They can contain more than 120 g/l of $Na_2TP$. The pH can be in the range 10 to 12.5 depending on the concentration of $Na_2TP$.

The process which is most frequently recommended for recovering $Na_2TP$ consists of acidifying the medium, in particular with sulphuric acid. The reduction in pH then causes $H_2TP$ to precipitate out, in a very considerable amount at pHs of less than 4.8, it being substantially complete at values of the order of 4.

However, recycling operations are only of interest industrially if the processes carried out can both recover the major portion of the reactants previously used in the polymerisation steps, in this case terephthalic acid ($H_2TP$) and the alkali metal hydroxide, in particular sodium hydroxide in the case of PTE recycling, and can produce them in a purity which is sufficient for direct re-use in new polymerisation steps. This is not often the case when $H_2TP$ is obtained by precipitation using sulphuric acid because of the presence in that $H_2TP$ of an excess of $SO_4^{2-}$ ions which is found in the form of sodium sulphate. Finally, the presence of traces of alkali metal salts, in particular $Na_2TP$ and $Na_2SO_4$, in the $H_2TP$ obtained constitutes a barrier to subsequent re-polymerisation of $H_2TP$.

The foregoing observations regarding the importance of recycling is of greater importance for $Na_2TP$ solutions such as those obtained by processes of the type described in the patents cited above, as they often contain an excess of the sodium hydroxide used in the previous saponification reaction. Thus such solutions must be neutralised first, in particular using sulphuric acid, so that the solution can initially be "screened" and filtered to eliminate solid waste. It is then generally purified further, for example by passage over activated charcoal. Thus the $H_2TP$ is recovered from such a "pre-purified" solution, usually by supplementary acidification of the medium, usually again with sulphuric acid as mentioned above. This process is thus accompanied by a loss in the total quantity of $Na^+$ species initially present in the form of sodium hydroxide, and their transformation into sodium sulphate which has only a low added value, let alone none not simply sent to refuse.

Is it actually possible to use the process proposed, for example, in U.S. Pat. No. 4,093,528 which employs electrolysis of such $Na_2TP$ solutions? A priori, the answer to that question can only be negative, as the yields on converting $Na_2TP$ to $H_2TP$ described in some of the examples of that patent are very low. Further, on repeating the experiment, insoluble non-conducting products are observed to form which rapidly block the access of other terephthalic ions to the anode and as a result, rapidly puts a stop to electrolysis.

In short, no economical process exists at present which can directly recover the major portion of the terephthalate and sodium ion species in a high degree of purity, in particular in the form of terephthalic acid and sodium hydroxide, from solutions of $Na_2TP$, especially when these are charged with impurities.

Thus the aim of the invention is to overcome these difficulties and provide a process for producing $H_2TP$ from solutions of its alkali metal salts, in particular $Na_2TP$, at a high degree of conversion.

A further aim is to produce other weak aromatic polycarboxylic acids under analogous conditions, which acids, like $H_2TP$, are insoluble in an aqueous acidic solution, and wherein the alkali metal salts of which, in particular the sodium salts, are soluble in an aqueous alkaline medium, and which can be polymerised in the presence of polyols, in particular ethylene glycol.

BRIEF DESCRIPTION OF THE DRAWINGS

FIG. 1 shows a skeleton diagram of an electrolyzer for electrolysing a $Na_2TP$ solution;

FIG. 2 is a graph showing the variation of amperage (A) (up the coordinate) as a function of time in minutes (along the abscissa), other conditions which cause modifications to this curve being explained below.

More particularly, the invention aims to provide an electrochemical method which is applicable to concentrated or even saturated aqueous solutions of these alkali metal salts, for example solutions containing more than 70 g/l, or even more than 120 g/l, of $Na_2TP$, which can thus be highly alkaline.

The term "weak acid" is used in the context normally employed in organic chemistry: it is an organic acid which is weakly dissociated in aqueous solution and thus its salts formed with a strong base such as sodium hydroxide form aqueous solutions where the pH of the solutions tend to be alkaline.

Having studied the causes of the poor yields of $Na_2TP$ to $H_2TP$ conversion in electrolysis studies of the type described in the United States patent cited above, the inventors have discovered that in an alkaline medium, the terephthalate ion undergoes a KOLBE reaction at the anode and loses a carboxy group by oxidation at the electrode surface. The radicals which are formed lead to the formation of dimers which co-precipitate at the anode, the presence of which has been monitored by infrared spectrometry. Such dimers are heavily involved in electrode blockage since, as will be shown below, the production of said insoluble and non conducting products tends to disappear as soon as the characteristic conditions of the process of the invention are employed.

The process of the invention, which can also be applied to the production of aromatic polycarboxylic acids which, like terephthalic acid, are insoluble in an aqueous solution, is started from an aqueous solution of an alkali metal salt of this acid, and is characterized by pre-acidification of the solution to bring the pH into a sub-precipitation pH range for the aromatic polycarboxylic acid and by electrochemical acidification of the pre-acidified solution in the anode compartment of an electrolysis cell.

Preferably, the respective anode and cathode compartments of the electrolysis cell are separated by cationic membranes which are permeable to alkali metal ions, to induce precipitation of the polycarboxylic acid at the anode. To separate the anode and cathode compartments, a diaphragm type microporous separator such as those used in industrial sodium hydroxide production cells can also be used. However, it has the disadvantage of a lower electrochemical yield for the production of sodium hydroxide and acid.

The expression "sub-precipitation pH range" as used in the present description means the pH range for which the most acidic pH value when applied to a solution of an alkali metal salt of the polycarboxylic aromatic acid under consideration leads to practically complete precipitation of the carboxylic acid in the medium.

Clearly, at the least acidic value of this pH range, dimer formation has already been avoided. It normally must not exceed 7. It should also be stated that in this pH range, any supplemental production of protons in the anode compartment is accompanied by precipitation of $H_2TP$ in the anode compartment, because of the electrochemical acidification of the solution.

The process of the invention is based on the discovery that, when applied to such a "pre-acidified" solution, electrolysis is essentially limited to that of the water in the $Na_2TP$ solution, the electrochemical reaction affecting the $Na_2TP$ molecules thus being substantially limited to the production of $HTP^-$ ions which are then directly convertible to insoluble $H_2TP$ following acidification of the medium under the effect of the production of protons liberated by the electrolysis of water, and the supplemental reduction in pH which occurs.

The invention thus exploits the fact that terephthalic acid is a weak acid with a solubility of $10^{-4}$ mole/l. The neutralisation-acidification equilibria are immediately displaced towards the insoluble $H_2TP$ acid form.

| AT THE ANODE | AT THE CATHODE |
|---|---|
| $H_2O \rightarrow \frac{1}{2} O_2 + 2H^+ + 2e^-$ | $2H_2O + 2e^- \rightarrow H_2 + 2OH^-$ |
| $Na_2TP + 2H^+ \rightarrow H_2TP + 2Na^+$ | $Na^+ + OH^- \rightarrow NaOH$ |

The $Na^+$ ions traverse the cationic membrane and protect it from precipitation of $H_2TP$ in contact therewith.

Purely for illustrative purposes regarding the sub-precipitation pH range, it can normally involve a variation of 2 to 3 pH units from the pertinent most acidic minimum value relating to the polycarboxylic acid under consideration.

In a variation, this sub-precipitation pH range can also be defined as corresponding to the pH range in which 10% to 90% by weight of the polycarboxylic acid salt initially employed is capable of subsisting in the form of negatively charged ions which are soluble in the medium.

For terephthalic acid, the sub-precipitation pH range can thus be of the order of 4 to 7, preferably in the range 5 to 6, and more particularly in the range 5.4 to 5.8.

Pre-acidification of the starting solution for which the pH of the medium is displaced towards the sub-precipitation range defined above can be carried out in a number of ways.

Starting from an alkaline solution, for example $Na_2TP$, the operation can be commenced by electrolysing it, it being noted, of course, that a rapid reduction in the electrolysis current will be observed with accumulation of insoluble products of the nature discussed above at the anode. This being the case, the onset of medium pre-acidification will be observed due to the production of protons liberated by electrolysis of water and transfer of $Na^+$ ions to the cathode compartment through the permeable membrane discussed above. Electrolysis can, however, be re-commenced by mechanically eliminating the first solid products formed (for example by scraping or brushing as will be described in the examples below) or by chemical elimination (for example by dipping the electrodes in a sodium hydroxide solution), these electrolysis and product elimination operations being repeated until the pH of the medium has dropped into the sub-precipitation range defined above. The experiment thus shows that at these pH values, the dimerisations discussed above no longer occur. The solid products formed at the anode are porous, so they no longer constitute an obstacle to the passage of current and, moreover, are readily separated

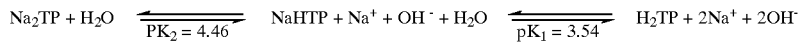

$$Na_2TP + H_2O \underset{PK_2 = 4.46}{\rightleftharpoons} NaHTP + Na^+ + OH^- + H_2O \underset{pK_1 = 3.54}{\rightleftharpoons} H_2TP + 2Na^+ + 2OH^-$$

The invention also exploits the fact that NaHTP anions are no longer oxidised at the electrode. There is no longer any competition from oxidation of the anion of the salt (and thus dimerisation, or destruction of these anions in the sub-precipitation pH range), so the protons liberated by the water molecule oxidation reaction can acidify the anion of the salt, which is accompanied by precipitation of insoluble $H_2TP$.

The electrochemical acidification reactions can be summarised by the chemical half reactions occurring at the anode (+) and cathode (−) respectively.

from the electrode when the water electrolysis operation, or electrochemical acidification, of the solution is continued.

While the above operations are sufficient to reduce the pH towards values in the sub-precipitation range even when the process of the invention is applied to very pure solutions of an aromatic polycarboxylic acid salt, because of the double contribution of the protons formed and the soluble anions derived from the carboxylic acid, the pre-acidification process can be accelerated by introducing an alkali metal salt of an electrochemically inert ion derived from a strong acid into the initial solution, which salt can contribute both to an increase in the conductivity of the solution and to an acceleration of the pre-acidification process.

The process of the invention is advantageously applicable to $Na_2TP$ solutions originating from saponification of alkylene polyterephthalates, in particular PTEs.

In addition to a high degree of conversion of $Na_2TP$ to $H_2TP$ in the process of the invention, the sodium hydroxide produced at the cathode is recycled, if necessary after prior concentration or even desiccation, to the step for saponification of fresh batches of PTEs. Similarly, the mother liquors from the anode compartment in the electrolysis equipment are also advantageously recycled to the step for dissolving the $Na_2TP$ formed at the end of the PTE saponification reaction in an aqueous phase, if this dissolution has not already been completed, and/or to the step for pre-acidification of the solution obtained.

The process of the invention is applicable with the same advantage to $Na_2TP$ solutions containing lower or higher proportions of $SO_4^{2-}$ ions, such as those obtained by carrying out conventional PTE saponification reactions and after prior purification operations of the type summarised above, which have a suitable conductivity before these solutions are introduced into the electrolysers, for example of the order of 20 to 60 mS/cm, in particular 30 to 50 mS/cm due to the amount of sodium sulphate already present. Further, these sulphate ions themselves already contribute to the pre-acidification operation mentioned above, which can if necessary be completed by adding measured quantities of sulphuric acid to the medium, so as to reach the sub-precipitation range indicated above.

The electrolysis reaction is more effective if the sodium ion concentration is kept at values in the range 10 to 20 g/l.

Electrolysis—or more exactly electrochemical acidification of the medium—is then carried out at a slightly acidic pH, which is nevertheless higher than that which would also cause substantial chemical precipitation of $H_2TP$ in the medium. It appears that the optimum conditions for electrolysis are met when the pH is such that it favours the formation of $HTP^-$ ions in the medium, in particular in a pH range of 5 to 6, in particular in the range 5.4 to 5.8.

In addition to producing high purity terephthalic acid at the anode, the crystallinity of the product obtained is observed to be higher, this crystallinity manifesting itself in the form of a higher degree of crystallinity and granulometry than those of terephthalic acid powders obtained by chemical precipitation, this crystallinity being more favorable to subsequent re-polymerisation of $H_2TP$ to PTE by reaction with a polyol, in particular ethylene glycol.

The maximum reactant recovery capacity starting from PTEs by alkaline saponification of the latter can be illustrated by the "global reaction" which can be written as follows:

GLOBAL REACTION

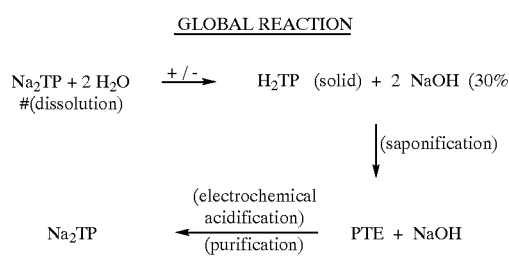

The quality of the results obtained and the conditions under which electrolysis can be carried out in a particularly effective manner are illustrated by the results of the experiments described below, The initial conditions (in the first three examples below) were respectively constituted by a synthesised disodium terephthalate and a disodium terephthalate (hereinafter termed "industrial $Na_2TP$") obtained from a composition which had been treated as follows:

a) previously ground PTE is intimately mixed with an excess with respect to the stoichiometric quantity (with respect to the equivalent of the terephthalic acid of PTE) of 2% to 10%, in particular 4% of hydrated sodium hydroxide;

b) the mixture obtained is heated to a temperature which is sufficiently low to prevent fusion of the starting materials and the alkali metal salt obtained;

c) the product obtained is dried at low temperature to eliminate the water initially contained in the starting materials, water of condensation and light alkylene derivatives so as to obtain a $Na_2TP$ which is easy to manipulate;

d) organic products such as diethylene glycol are eliminated by vacuum distillation;

e) an aqueous solution of $Na_2TP$ is formed and sulphuric acid is added to adjust the pH to a value close to neutral;

f) the solution is screened (elimination of solid particles), filtered and purified over activated charcoal.

The solution obtained after this treatment is that termed industrial $Na_2TP$.

The electrolysis equipment used is shown in diagrammatic form in FIG. 1. Its operation can be summarised as follows.

Anode Compartment—Acidification of $Na_2TP$

The $Na_2TP$ (sodium terephthalate) solution is introduced unchanged into the anode compartment CA° of the electrolysis cell. This solution is that obtained by dissolving a synthesised product or industrial $Na_2TP$ in water. A circulating pump ensures transfer of a buffer volume from reservoir T3 to the electrolysis cell. The solution is introduced into the bottom of the cell. The liquid returned to the buffer reservoir by overflowing from the top of the cell.

A lead anode is initially used for the first part of the experiment. For the other parts, a platinated titanium anode, an expanded titanium anode activated with iridium oxide and ruthenium, and a platinated niobium anode are used respectively.

Cathode Compartment—NaOH Formation

The two cathode compartments (CC1 and CC2) are located either side of the central anode compartment. A selectively cationic NAFION (or any other selective cation exchange membrane) type ion exchange membrane separates each cathode compartment from the anode compartment.

The membranes are installed in the electrolyser (or in cassette mountings) after pre-treating for two hours by immersion in a 1.0% to 5% sodium hydroxide solution, for example 5% by weight. They are of a suitable size to form a tight seal between the compartments when installed in the electrolyser. A further method for conditioning them consists of immersing them for two hours in said sodium hydroxide solution containing 40 g/l of NaOH.

The initial solution used in the cathode compartments is stored in buffer reservoirs (T1+T2); it is composed of 0.1 M sodium hydroxide. Transfer between T1 and CC1 is by means of a magnetic pump. Return is by overflow. Catholyte transfer between T2 and CC2 was by the same means.

The cathodes are stainless steel plates or any other suitable material with a flat geometry, or of non perforated expanded metal.

Current Source

A continuous 10 V–10 A current source is used for the experiment.

EXAMPLES OF EXPERIMENTS

Example 1

Preparation of Terephthalic Acid by Acidification of a Synthesised $Na_2TP$ Solution (Merck)

The test cell illustrated in FIG. 1 was installed. A volume of 3 litres of $Na_2TP$ solution (70 g/l) was prepared (solution A) from a commercially available synthesised product. Electrolysis of this solution was begun, the solution having been prepared with an analytical product. The current rapidly fell from 3 amps to 0.1 amps. Since cleaning the electrode did not boost the electrolysis current (or only to very low values (0.5 A), it was decided to cease electrolysis of this solution.

It appears that three factors must be combined to ensure proper electrolysis:
1. The conductivity of the solution.
2. The electrolysis pH.
3. The concentrations of the ionic species in solution.
1. Demonstration of the Relative Importance of the Conductivity and pH of the Solution The conductivity values measured in the different solutions are shown in TABLE I below.

TABLE I

Conductivities of different solutions

| CONDUCTIVITIES | mS/cm | T, °C. |
|---|---|---|
| Synthesised $Na_2TP$ solution, 70 g/l | 32.8 | 24 |
| $Na_2SO_4$ solution, 5.0 g/l | 6.7 | idem |
| Synthesised solution, $Na_2TP$ (70 g/l) + $Na_2SO_4$ (5.0 g/l) | 36.9 | Idem |
| Reminder: Industrial $Na_2TP$ solution | 38 | 22 |
| CATHOLYTE NaOH solution – 0.1 N | 17.4 | 24 |

The conductivity of the solution was measured during its preparation. For the synthesised solution (solution A), conductivity values of 32 mS/cm (millisiemens/cm) were found, comparable to those of an industrial $Na_2TP$ solutions and a synthesised $Na_2TP$ solution to which $Na_2SO_4$ had been added in a concentration of 5.0 g/l (36 to 38 mS/cm)—(solution B). These values were much higher than those of a 5.0 g/l sodium sulphate solution, namely 6.0–7.0 mS/cm.

Adding $Na_2SO_4$ could thus increase the conductivity of the synthesised $Na_2TP$ solution. However, it was established that this increase in conductivity could not result in effective production of terephthalic acid.

It was observed that during the entire period when the electrolysis current was passed, the conductivity of the solution remained substantially stable. However, during the initial electrolysis period, the electrode had to be cleaned frequently to renew the active surface of the electrode. The cell current had a saw-tooth profile as shown in FIG. 2. From an analysis of these elements, then, it appears that regulating only the conductivity of the solution cannot of itself ensure that the optimal electrolysis conditions are produced.

2. pH

A particular feature of the invention is constituted by the fact that the pH has been shown to be the important, if not determining, element in the $H_2TP$ formation kinetics after one hour of electrolysis. It was shown that under otherwise identical conditions, adding a solution of $H_2SO_4$ in a quantity equivalent to a tenth of the $Na_2TP$ concentration produced a remarkable improvement in the electrode conditions.

This addition of sulphuric acid did not affect the conductivity of the solution which remained at a value close to 36.0 to 38.0 mS/cm.

In contrast, the pH of the solution had fallen from 6.5 to 5.7. While slight, this difference in pH was shown to be sufficient to optimise the current and quality of the precipitate formed in the electrolysis. At the start of electrolysis, the precipitate adhered to the electrode. Frequent scraping was required (every 10 minutes). When a third of the acidification had been achieved, the precipitate increased substantially to a 5 to 10 mm thick layer perpendicular to the electrode. It then detached easily and the current stability was substantially improved (see the second portion of the curve in FIG. 2).

3. Concentration of Species in Solution

The following phenomena occur in the solution:
1) Reduction in the concentration of the $TP^{2-}$ anion because of $H_2TP$ precipitation.
2) Reduction in the $Na^+$ concentration, due to transfer through the membrane to form sodium hydroxide.
3) $SO_4^{2-}$ concentration maintained.
4) Slow evolution of pH and thus of $H_3O^+$ concentration.

It was estimated that the monosodium salt $HTP^-$ was also formed which was predominant in the intermediate pH range between 6 and 4, according to the ionic dissociation equilibria described above. All of these observations agreed with the conclusion that the acid $H_2TP$ is formed most effectively in the pH range in which the $HTP^-$ species tended to be formed. It is this which appears to contribute mainly to optimum $H_2TP$ formation.

Example 2

A $Na_2TP$ solution was prepared with a synthesised product. A quantity of sulphuric acid equivalent to half the initial quantity of $Na_2TP$ was added. A cell current of 5.0 amps was produced with a tension of 8.0 to 10.0 V at the start of the experiment. The pH of the solution was about 5.4 to 5.8. The conductivity of the solution was 40.2 mS/xm. The experiment was carried out using a titanium-IrOx-RuOx electrode. Using this electrode, the electrolysis conditions became normal and in order to regain the initial current, the terephthalic acid layer was cleaned off regularly.

Under these conditions, the current drop was no longer observed; the acid layer increased over the whole of the electrode surface. It was more than 5.0 mm thick on each side of the electrode. It was porous and did not prevent the current from passing and contributed to the regular production of acid.

Given the surface area of the membranes used in the experiment (44 cm$^2$) and the average current (4.0 to 5.0 A), the estimated current density was of the order of 5.0 to 10.0 A/dm$^2$.

Example 3

Preparation of Terephthalic Acid by Acidification of an Industrial $Na_2TP$ Solution An industrial $Na_2TP$ solution was prepared. A quantity of sulphuric acid equivalent to half of the initial quantity of $Na_2TP$ was added. At the start of the experiment, a cell current of 5.0 amps was obtained with a tension of 8.0 to 10.0 V. The pH of the solution was about 5.4 to 5.8. The experiment was carried out using a titanium-IrOx-RuOx electrode. Using this electrode, the electrolysis conditions became normal and in order to regain the initial current, the terephthalic acid layer was cleaned off regularly.

The same reproducibility of results was observed using the industrial $Na_2TP$ solution as with those obtained by electrolysis of the synthesised $Na_2TP$ solution. The conductivity of the industrial $Na_2TP$ solution (38 mS) was higher than that of the synthesis $Na_2TP$ solution (32 mS ($Na_2TP$)). The sulphate concentration in the industrial $Na_2TP$ solution was equivalent to 5.0 g/l.

The electrochemical equivalent of the $H_2TP$ was 3.09 g/Ah. The calculation for the $H_2TP$ formation yield is shown in Table II below. It appears that 86.4% of the theoretical value of the $Na_2TP$ present in the starting solution was transformed by electrochemical acidification.

TABLE II

EVALUATION OF QUANTITIES OF $H_2TP$ RECOVERED DURING TESTS

| Parameters | Quantity, grams | Method |
|---|---|---|
| Start | | Titration |
| 70 g/1 × 1.81 = | 126.0 $Na_2TP$ | |
| i.e., equivalents of $H_2TP$ | 99.6 $H_2TP$ | |
| Total recovered - formed at electrode | 76.0 $H_2TP$ | Weighing |
| Solid precipitated by $H_2SO_4$ | 10.0 $H_2TP$ | Weighing |
| Total = | 86.0 | |
| Difference - | 99.6 − 86 = 13.6 | |
| Total | i.e., 13.6 | |
| Degree of transformation of $Na_2TP$ to $H_2TP$ | 86.4% | |

Example 4

A solution of $Na_2TP$ was prepared by dissolving a recrystallised salt. The concentration was 120 g/l of $Na_2TP$. The conductivity of this solution was 45.0 mS/cm, at a temperature of 20° C. The pH of this solution was 10.5.

The solution was electrolysed using a titanium-platinum electrode which could be cleaned easily. The electrolysis cell comprised two compartments separated by a cationic membrane. Terephthalic acid production occurred at the anode while sodium hydroxide was produced at the cathode.

The cell current was 5.0 amps for an electrode surface of 0.5 $dm^2$. After half an hour of electrolysis, the cell current dropped to a value of less than 1.0 A. A white film covering the surface was seen to form on the electrode. Since this film was non conducting, it constituted a barrier to the passage of current.

Simple brushing of the electrode or immersion in concentrated sodium hydroxide could clean the electrode. After this cleaning operation, electrolysis could be resumed under normal conditions. However, after a certain time, the same phenomenon of blocking the electrode by a non conductive film occurred again.

The electrode washing operations were repeated. Each of the above operations was accompanied by a reduction in the pH of the medium.

When the pH of the electrolysis solution fell below 7.0, an insoluble, non conducting film no longer formed at the anode. At this moment, electrolysis could occur under normal conditions, at a constant current, without blocking the electrode.

Thus in solutions of $Na_2TP$ with an equivalent concentration of 96.0 g/l and up to about 24.0 g/l, terephthalic acid can be continuously produced by the electrochemical method, ensuring, of course, that the anode compartment is re-supplied with $Na_2TP$ at the same rate as $H_2TP$ is precipitated at the anode, while keeping the pH at a value below 7.0.

Thus it was possible to produce a quantity equivalent to 750 g of $H_2TP$ by electrochemical acidification in a ten litre volume of solution containing 90 to 100 g/l of $Na_2TP$ by passing a current of 10 amps through the cell.

Example 5

During continuous production of terephthalic acid by electrochemical acidification, the electrolysis cell was supplied with a volume of $Na_2TP$ solution in a concentration of 70.0 to 85.0 g/l. The pH of this solution was adjusted to 7.0±0.5 by electrochemical acidification as described in Example 1 above.

This solution was electrolysed using a current of 10 amps and after passing the current for one hour, a quantity equivalent to 26.0 grams of $H_2TP$ had been produced, corresponding to an electrochemical yield of about 85%.

In order to continue electrolysis under the best pH and conductivity conditions, a quantity of crystalline $Na_2TP$ was introduced into the solution. This quantity was equivalent to the quantity previously extracted by electrochemical acidification, in this instance 32.0 grams of $Na_2TP$. Electrolysis was continued and then continuously produced terephthalic acid from a sodium terephthalate solution wherein the concentration had been kept constant by regular additions of solid $Na_2TP$.

Example 6

A $Na_2TP$ solution was prepared by dissolving a re-crystallised salt; the concentration of $Na_2TP$ was 120 g/l. A quantity of sodium carbonate equivalent to 5.0 g/l was added. The conductivity of this solution was 45.0 to 50.0 mS/cm; the temperature was 20° C. The pH of this solution was over 11.0.

The solution was electrolysed using a titanium-platinum electrode which could be cleaned easily. The electrolysis cell comprised two compartments separated by a cationic membrane.

The cell current established itself at 5.0 amps for an electrode surface area of 0.5 $dm^2$. When the pH of the electrolysed solution was less than 7.0, electrolysis could be carried out under normal conditions, at a constant current, without blocking the electrode.

Thus in solutions of $Na_2TP$ in a concentration equivalent to more than 100.0 g/l and up to about 24.0 g/l, terephthalic acid could be continuously produced using the electrochemical method. In this case, the sodium carbonate acted as an electrolyte support, in a similar manner to sodium sulphate which could be used for the same function.

The following observations can be made regarding the three above examples.

(1) NaOH concentration. The sodium hydroxide used in the cathode compartment was analysed at the start and end of the operation. The concentration was determined by titration with sulphuric acid. It changed from 0.1 M to 1.0 M during electrolysis. An 85% yield was obtained for sodium hydroxide formation by an electrochemical route (see Table III below).

TABLE III

Development of NaOH concentration in the cathode compartment.

| Parameters | Concentration (g/l) | Conductivity (mS/cm) | |
|---|---|---|---|
| | | | Quantity of NaOH produced by electrolysis (grams) (1) |
| NaOH - t = 0 | 3.8 | 17.4 | |
| NaOH - t = 8h30 | 39.8 | 199.5 | |
| Difference | 36.0 | | 36 |
| | Theory q NaOH/Ah | Total Ah (FIG. II) | Theoretical total (2) |
| Electrochemical equivalent | 1.49 | 28.5 | 42.46 |
| Electrochemical production yield (2)/(1) × 100 | | | 85% |

(2) A preliminary granulometric analysis revealed a different granulometric distribution for $H_2TP$ samples produced by chemical neutralisation ($H_2SO_4$) and by electrochemical acidification. The distribution curves for samples produced by electrochemical acidification revealed in this case that the proportion of grains with sizes of at least 10 microns was substantially higher than that of the samples produced by chemical neutralisation; in contrast, the proportion of particles with sizes less than 1.0 micron was much smaller.

The invention is not limited to a process for electrochemical acidification of a sodium terephthalate solution. It encompasses electro-acidification of terephthalates other than those of alkali metals, in particular potassium terephthalate, when the saponification reaction described above is carried out with potassium hydroxide.

In the same manner, the invention can be applied to the recovery of other aromatic polycarboxylic acids which, like terephthalic acid, can be obtained in an insoluble state by electro-acidification of solutions of these salts, in particular sodium salts, in the anode compartment of an electrolysis cell.

Examples of such aromatic polycarboxylic acids which can be mentioned are:
  isophthalic acid;
  naphthalenedicarboxylic acids, in particular 2,6-naphthalenedicarboxylic acid;
  4,4-oxybis(benzoic) acid;
  5-ter-butyl-1,3-benzenedicarboxylic acid.

What is claimed is:

1. A process for producing a weak aromatic polycarboxylic acid which is insoluble in an aqueous acidic solution and which is polymerizable in the presence of a polyol, wherein said weak aromatic acid is one whose salts of alkaline metals are soluble in an alkaline solution above a pH of 7, which process comprises pre-acidifying an aqueous solution of an alkaline metal salt of said acid to bring the pH into a sub-precipitation pH range of said aromatic polycarboxylic acid, and electrochemically acidifying the pre-acidified solution in an anode compartment of an electrolysis cell, to induce precipitation of said aromatic polycarboxylic acid at the anode.

2. The process of claim 1 wherein said salt of alkaline metal is a sodium salt.

3. The process of claim 1, which is carried out in said electrolysis cell comprising said anode compartment and a cathode compartment, and wherein said anode compartment and said cathode compartment are separated by cationic membranes which are permeable to alkaline metal ions.

4. The process of claim 3, which comprises carrying out the pre-acidification electrochemically directly in the electrolysis cell, eliminating mechanically or chemically the first precipitates formed at the anode, repeating these operations until the electrolysis current is substantially stabilised at a pH within said sub-precipitation range.

5. The process according to claim 4, which is carried out continuously, and wherein the anode compartment of the electrolysis cell is supplied with new charges of aromatic polycarboxylic acid salt in proportion to the quantity of aromatic polycarboxylic acid precipitated at the anode while ensuring that the pH of the medium is kept within the sub-precipitation range.

6. The process of claim 3, wherein said cathode compartment is fed with a solution of a hydroxide of an alkaline metal, wherein said alkaline metal derives at least in part from said salt of said aromatic polycarboxylic acid.

7. The process of claim 6, wherein the alkaline metal is sodium and the sodium ion content in the hydroxide solution is more than 0.1 M.

8. The process of claim 1, which comprises pre-acidifying said aqueous solution of the alkaline metal salt which is concentrated or saturated with said salt.

9. The process of claim 8, wherein the aqueous solution of the alkaline metal salt which is pre-acidified, is a solution produced by saponification of an aromatic polycarboxylate of a polyol, which comprises recycling the aromatic polycarboxylic acid produced to a production step of new batches of said aromatic polycarboxylate of a polyol, and recycling the base produced in the cathode compartment to the saponification step of new batches of said aromatic polycarboxylate of said polyol, and recycling a mother liquor from the anode compartment to a dissolution step of an alkaline metal polycarboxylate resulting from saponification, if such dissolution is not already complete, or to the pre-acidifying step of said aromatic polycarboxylate, or bath.

10. The process of claim 1, wherein said sub-precipitation pH range is of the order of 2 to 3 pH units from the most acidic pH value below which said aromatic polycarboxylic acid at the anode is caused to undergo substantially complete precipitation at the anode.

11. The process of claim 1, wherein said sub-precipitation pH range extends from the pH value which authorizes 10% by weight to the pH value which authorizes 90% by weight of the initial weight of a salt of said polycarboxylic acid to remain in solution.

12. The process of claim 1, wherein the aromatic polycarboxylic acid is a phthalic acid.

13. The process of claim 12 wherein the aromatic polycarboxylic acid is terephthalic acid.

14. The process of claim 13, wherein the solution of the alkaline metal salt of said terephthalic acid is pre-acidified to a pH in the range from 4 to 7.

15. The process of claim 14, wherein the solution of the alkaline metal salt of said terephthalic acid is pre-acidified to a pH in the range from 5.4 to 5.8.

16. The process of claim 15, wherein the initial concentration of the alkaline metal terephthalate in said solution ranges from 70 g/l to 120 g/l.

17. The process of claim 12, wherein the solution of the alkaline metal salt of said phthalic acid is pre-acidified to a pH in the range from 4 to 7.

18. The process of claim 1, which comprises introducing into the solution of the alkaline metal salt of the aromatic polycarboxylic acid electrochemically inert anions to increase the conductivity of the electrolyte.

19. The process of claim 18, wherein the electrochemically inert anions are selected from those which also contribute to the pre-acidification of the solution of the alkaline metal salt of the aromatic polycarboxylic acid.

* * * * *